(12) United States Patent
Pierart

(10) Patent No.: US 11,998,325 B2
(45) Date of Patent: Jun. 4, 2024

(54) BODY-MONITORING SYSTEM WITH SEPARABLE LINK

(71) Applicant: PKvitality, Paris (FR)

(72) Inventor: Luc Pierart, Villejuif (FR)

(73) Assignee: PKvitality, Paris (FR)

( * ) Notice: Subject to any disclaimer, the term of this patent is extended or adjusted under 35 U.S.C. 154(b) by 671 days.

(21) Appl. No.: 17/265,408

(22) PCT Filed: Aug. 2, 2019

(86) PCT No.: PCT/EP2019/070946
§ 371 (c)(1),
(2) Date: Feb. 2, 2021

(87) PCT Pub. No.: WO2020/025821
PCT Pub. Date: Feb. 6, 2020

(65) Prior Publication Data
US 2021/0267508 A1 Sep. 2, 2021

(30) Foreign Application Priority Data
Aug. 3, 2018 (EP) ..................................... 18306066

(51) Int. Cl.
A61B 5/145 (2006.01)
A61B 5/00 (2006.01)
A61B 5/1473 (2006.01)

(52) U.S. Cl.
CPC ...... *A61B 5/14546* (2013.01); *A61B 5/14514* (2013.01); *A61B 5/681* (2013.01);
(Continued)

(58) Field of Classification Search
CPC . A61B 5/14546; A61B 5/14514; A61B 5/681; A61B 5/685; A61B 5/1473;
(Continued)

(56) References Cited

U.S. PATENT DOCUMENTS

2021/0275097 A1* 9/2021 Pushpala .............. A61B 5/1495

FOREIGN PATENT DOCUMENTS

| CN | 108310615 A | 7/2018 |
|---|---|---|
| EP | 3 293 603 A1 | 3/2018 |

(Continued)

OTHER PUBLICATIONS

European Search Report dated Jan. 2, 2019 in European Application No. 18306066.4.
(Continued)

*Primary Examiner* — Eric F Winakur
*Assistant Examiner* — Abid A Mustansir
(74) *Attorney, Agent, or Firm* — Sughrue Mion, PLLC

(57) ABSTRACT

A body-monitoring system (1), intended to be attached to a limb of a living being, having a first module (100) having fastening and clamping mechanisms (110) configured to hold and clamp the system (1) on a limb; a second module (200) having microneedles (210) configured to be inserted into the skin in order to sample and/or analyse a bodily fluid of the wearer of the body-monitoring system (1) when positioned on the limb, the two modules (100, 200) being able to be coupled together in position by a complementarity of shape. The first module (100) and the second module (200) are connected together by a separable link (300), the separable link being configured to be released when a tearing threshold is exceeded, the link also being reusable.

19 Claims, 2 Drawing Sheets

Figure 1:
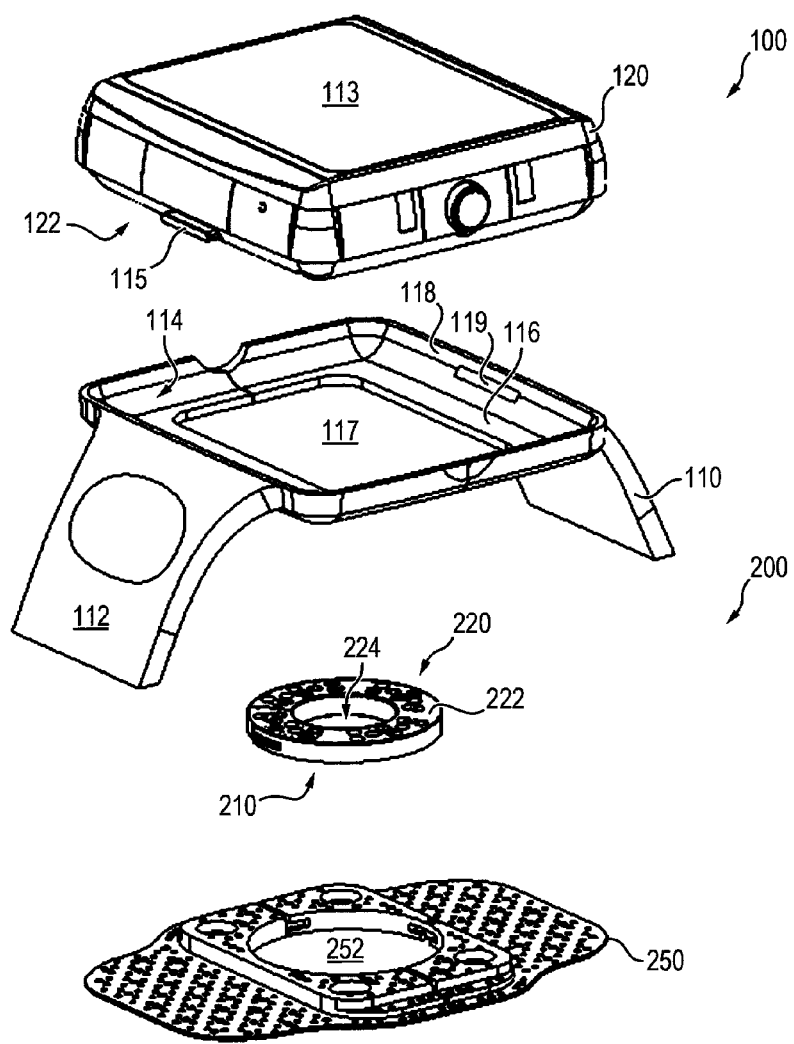

(52) U.S. Cl.
CPC ............ *A61B 5/685* (2013.01); *A61B 5/1473* (2013.01); *A61B 2560/0406* (2013.01); *A61B 2560/0443* (2013.01); *A61B 2560/0456* (2013.01)

(58) Field of Classification Search
CPC .... A61B 2560/0406; A61B 2560/0443; A61B 2560/0456; A61B 2505/07; A61B 5/14532; A61B 5/6824; A61B 5/6831; A61B 5/6832; A61B 5/6839; A61B 5/688; A61B 5/6882
See application file for complete search history.

(56) References Cited

FOREIGN PATENT DOCUMENTS

| WO | 2015/127218 A1 | 8/2015 | |
|---|---|---|---|
| WO | 2018/104647 A1 | 6/2018 | |
| WO | WO-2018104647 A1 * | 6/2018 | ......... A61B 5/14514 |

OTHER PUBLICATIONS

International Search Report dated Sep. 9, 2019 in International Application No. PCT/EP2019/070946.
Written Opinion of the International Searching Authority dated Sep. 9, 2019 in International Application No. PCT/EP2019/070946.

* cited by examiner

BODY-MONITORING SYSTEM WITH SEPARABLE LINK

CROSS REFERENCE TO RELATED APPLICATIONS

This application is a National Stage of International Application No. PCT/EP2019/070946, filed Aug. 2, 2019, claiming priority to European Patent Application No. 18306066.4, filed Aug. 3, 2018.

GENERAL TECHNICAL FIELD

The present invention concerns a body monitoring system via body, typically interstitial, fluid analysis using microneedles.

More specifically, the present invention concerns the management of the holding of the microneedles in the skin.

STATE OF THE ART

Some pathologies such as diabetes require daily monitoring of biochemical parameters of the human body, i.e. concentrations of some compounds (glycemia in the example of glucose).

To this end, it is common to prick a point of the skin so as to bead up a drop of blood, and to analyze this drop either reactively (for example with a strip) or electronically (for example by at least one analytical sensor), so as to estimate the target parameter(s).

Much less invasive advanced systems are known today, which simply analyze the interstitial fluid, that is to say, the fluid that fills the space between blood capillaries and cells. It has indeed an ionic composition close to that of blood plasma.

These advanced systems thus allow monitoring the desired biochemical parameters transcutaneously that is to say without the need to evenly pierce the skin and take samples.

Devices with microneedles are known, which have the advantage of being less invasive than conventional needles. However, it is important that these microneedles remain in place.

There are for that purpose indwelling devices where microneedles are held on the skin with an adhesive tape. However, it is desirable to be able to carry out a continuous or quasi-continuous control, which requires autonomous devices. The GlucoWatch device, which used iontophoresis (and not needles) can be cited.

The device is also known from document WO2018104647, which has a casing comprising a removable capsule, the capsule accommodating microneedles configured to sample interstitial fluid. The casing, for its part, accommodates most part of the electronics.

This portable device, typically on the wrist, allows continuous measurement and it suffices to change the capsule in order to change microneedles.

However, when such a device is worn on the wrist or on another limb, there is a risk of tearing the microneedles when the device is snagged by a sleeve, a door, a chair, etc. This tearing is not acceptable in terms of pain and skin integrity.

In addition, it is important that the device is easy to use.

PRESENTATION OF THE INVENTION

In order to address some of these issues, the invention proposes, in a first aspect, a body analyte monitoring system intended to be attached to a limb of a living being, comprising:

a first module, comprising attachment and tightening means configured to hold and tighten the system on a limb, a second module, comprising microneedles configured to be inserted into the skin to sample and/or analyze a body fluid from the wearer of the body monitoring system when the latter is positioned on the limb, the two modules being able to be in coupled position where they are coupled together by shape complementarity, the system being characterized in that the first module and the second module are interconnected by a separable link, the separable link being configured to be released when a tearing threshold is exceeded, the link being also reusable, the threshold of tearing of the separable link being lower than the threshold of tearing of the microneedles from the skin, so that once worn, a tearing force disengages the separable link to prevent the tearing of the microneedles from the skin.

The separable link is disengaged by tearing, that is to say an essentially translational movement. The tearing threshold is low. For example, a value comprised between 30 and 400 g of tearing threshold is suitable (by mass) or a value comprised between 0.3 and 4 N is suitable (by weight), that is to say a mass or weight greater than the predefined threshold applied in tearing allows separating the two modules. Preferably, a value comprised between 70 and 250 g or 0.7 and 2.5 N is chosen.

Particularly, the body monitoring system is configured to switch:

from a coupled position, in which the first module and the second module are secured to each other thanks to the separable link, and can exchange electrical signals and/or fluid, to a free position, in which the first module and the second module are not in coupled position.

In one embodiment, the first module further comprises a casing, to which the attachment and tightening means are attached.

The attachment and tightening means may comprise a receptacle for the casing, the casing being removably attachable in the receptacle.

In one embodiment, the casing is attachable to the second module by the separable link.

In one embodiment, the second module comprises a capsule, which itself comprises the microneedles and comprises a patch attachable to the capsule.

The patch then has a skin-adhesive power (either by its own material or by the addition of an adhesive layer).

In one embodiment, the patch is securable to the first module by the separable link.

In one embodiment, the patch is removably secured to the capsule, in order to be able to change the patch while keeping the same capsule.

In one embodiment, the patch has an annular shape surrounding the capsule, the capsule comprising a protrusion configured to cooperate with a notch in the patch.

In one embodiment, the threshold of tearing of the microneedles takes into account the adhesive function of the patch.

In one embodiment, the attachment and tightening means comprise a strap, for example made of elastic material and/or for example in the form of an adjustable bracelet.

In one embodiment, the strap is sandwiched between the capsule and the casing.

In one embodiment, the strap is independent of the casing and ensures the tightening to the limb independently of the casing.

In one embodiment, the separable link comprises a magnet. The magnet is located in the first or the second module, or even both (for a stronger link).

In one embodiment, the separable link comprises a clipping.

In one embodiment, the system further comprises at least one guide between the first module and the second module, the guide being configured to allow a natural return to the coupled position.

At least one of the guides may comprise a cylindrical or frustoconical shape comprised in the first module and a preferably funnel-shaped complementary opening in the second module, the guide allowing defining an intermediate position. The frustoconical shape is then partially or totally engaged in the complementary funnel-shaped opening.

In one embodiment, the wedging between the patch and the bracelet acts as a guide in a plane, by preventing the rotation (the frustoconical part allowing guidance in an orthogonal plane but without necessarily blocking the rotation along this axis).

In one embodiment, the casing comprises a frustoconical shape (preferably of revolution) and the capsule comprises a flared through opening, of complementary shape.

In one embodiment, the casing comprises a battery and/or a processor for the management of the data of the sensor, in particular.

In one embodiment, the system comprises complementary electrical connectors on the first module and the second module (200). Alternatively, information exchanges between the two modules can be done wirelessly, using a wireless connection between the two modules.

The first aspect of the invention also proposes a body analyte monitoring kit comprising a body monitoring system and a dock configured to receive, at least partially, the first module of the body monitoring device, and preferably to receive the casing. The link between the dock and the monitoring system is preferably a separable link that uses elements of the separable link between the first module and the second module. Advantageously, magnets are used.

According to a second aspect of the invention, a body monitoring system is proposed, intended to be attached to a limb of a living being, comprising:
  a first module, comprising:
    a casing comprising a battery and/or a microprocessor, and attachment and tightening means configured to hold and tighten the system on the limb,
  a second module, comprising:
    a capsule comprising microneedles configured to be inserted into the skin to sample and/or analyze a body fluid from the wearer of the body monitoring system when the latter is positioned on the limb,
    a patch with a skin-adhesive power,
  in which:
    the two modules are removably detachable from a coupled position where they are coupled together by shape complementarity,
    the casing is removably detachable from the attachment and tightening means,
    the patch is removably detachable from the capsule.

Preferably, the first module and the second module are interconnected by a separable link configured to break when a threshold of tearing of the microneedles is exceeded. The separable link has been described previously.

Preferably the separable link is done between the patch and the casing.

The different embodiments presented for the second aspect apply to the first aspect.

PRESENTATION OF THE FIGURES

Figure 2:
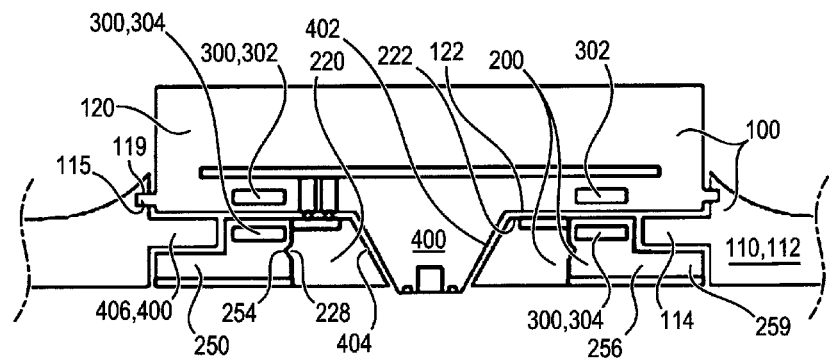
Figure 3:
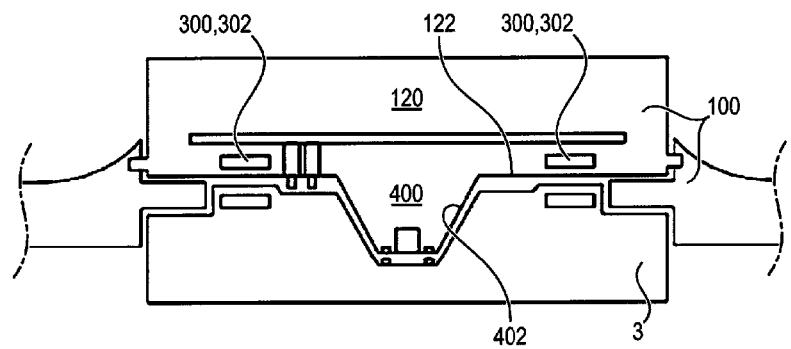
Figure 4:
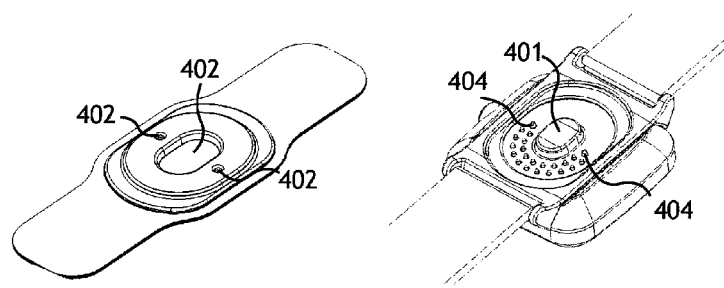

Other characteristics and advantages of the present invention will become apparent upon reading the following description of a preferred embodiment. This description will be given with reference to the appended drawings in which:

FIG. 1 illustrates an exploded view of a bracelet, a casing, a capsule and a patch as usable in the framework of the invention, FIG. 2 illustrates a diagram representing a system comprising a bracelet, a casing, a capsule and a patch secured to the capsule and attached to the casing, according to one embodiment of the invention, FIG. 3 illustrates a diagram representing a bracelet and a casing, mounted on a recharging dock (or base), FIG. 4 illustrates the guidance of the casing in the capsule.

DETAILED DESCRIPTION

General Architecture

With reference to FIGS. 1 to 3, the present invention concerns an electronic body monitoring system 1. It is an improvement in the device from document WO2018104647. Consequently, the invention falls within the same general concept of an autonomous integral system with low pain and low hygiene risk which is reusable.

By "body monitoring" is meant the verification of biochemical constants of a person wearing the system 1, typically the concentration of a protein, a hormone, a marker, oxygen, nutrients, etc., in the interstitial fluid of the person. The example of glycemia can be cited. Those skilled in the art will be able, if necessary, to monitor other physical body quantities such as lactate, hydration etc.

The description will be illustrated with interstitial fluid but applies to the other body fluids such as blood.

The system 1 is said to be autonomous because it does not require the use of additional equipment.

The system 1 is intended to be attached to a limb of a living being, typically an arm or a leg of a human being. The preferred attachment area is the wrist where the system 1 is similar to a watch.

The system 1 is formed of two modules 100, 200 interconnected by a separable link 300 which is reusable. A coupled position and a free position are thus defined. In the coupled position, the two modules 100, 200 are not physically separated and can exchange data. It is thus possible to handle the system as a secured whole, provided that no force above a tearing threshold is exerted, which allows dissociating the two modules 100, 200. In the coupled position, there is preferably no possible freedom of movement between the two modules 100, 200.

The first module 100 comprises in particular means for attaching and tightening 100 the system 1 to a limb and the second module 200 comprises in particular microneedles 210 configured to be inserted into the skin (in a superficial part of the epidermis). These microneedles 210, when the first module 100 is in position on the limb, allow sampling and/or analyzing a body fluid, as mentioned above. In the case of pierced microneedles forming a channel in each microneedle, a sample can be taken by fluidly connecting a system for pumping the interstitial fluid to the channel, or simply by capillarity. An analysis system may comprise microneedles each provided with an electrode or a set of electrodes, or be offset after the microneedles, so as to cause an electrochemical reaction adapted to detect an analyte in the interstitial fluid. The microneedles 210 are disposed on a contact face of a capsule 220 which can engage with the first module 100.

The microneedles 210 advantageously consist of an array of microneedles 210 in contact with the skin when the first module 100 is placed on the body of a person. The microneedles 210 can therefore be either hollow, to sample fluid, or full, to analyze the fluid directly. In the first case, typically, the microneedles 210 allow the extraction of interstitial fluid from the dermis painlessly without beading up blood, and send it to a sensor present in the system 1 (more specifically preferably in the second module 200). In the second case, the microneedles 210 do not sample any fluid and integrate the sensor on their surface, in the form of a biochemical material able to react with the analyte desired be measured in the fluid.

Preferably, said microneedles 210 comprise between four and fifty, substantially pyramidal, microneedles with tips of a height comprised between 100 μm and 1,000 μm, preferably 0.3 mm and 0.8 mm. Each of these advantageous characteristics of the microneedles can be taken separately or in combination with the other ones.

The two modules 100 and 200 each have a coupling face 122, 222, of complementary shape, which allows placing the second module 200 in a location for accommodating the first module 100. They are therefore in contact with each other.

Finally, the first module 100 and the second module 200 are configured to be coupled by the separable link 300. This link 300 secures the two modules 100, 200 as long as a tearing threshold is not exceeded. Once the link is deactivated, it can be reactivated: it is not a one-time-use link, but a removable link, reusable an indefinite number of times.

Thus, the second module 200 is designed to be positioned on the skin, with the microneedles 210 which remain inserted into the skin, regardless of the movements of the first module 100: either they are voluntary movements of separation of the two modules 100, 200, or they are involuntary movements of everyday life which tend to separate the two modules 100, 200 (blocking of the first module in a door, a sleeve, a blow received involuntarily, etc.). This avoids the tearing of the microneedles 210 in all these situations, since the separable link 300 will break before the microneedles 210 are torn from the skin.

As illustrated in FIGS. 1 to 3, the first module 100 further comprises a casing 120 in which are disposed data processing means (particularly a processor or a microcontroller) configured to process measurements acquired by the sensor, and where appropriate, data storage means (in particular a memory, particularly of the flash type, and/or the memory of the microcontroller) allowing for example storing these measurements, and/or a date of the first use of each sensor to calculate an expiry date of the sensor(s) (the biochemical sensors have a limited lifespan). The data processing means are also used to generate instructions towards various components. In the framework of this description, these different functions are performed by the same unit. However, it is possible to provide for dedicated processors. The system also comprises a battery, advantageously a rechargeable battery, for the electrical supply to the components, for example via a port (understood as also being able to be used to connect the system 1, for example to a computer for downloading the acquired and/or processed data).

Preferably, the system 1 can comprise wireless connection means (particularly of the WiFi but also Bluetooth or even 3G/4G type) for a connection to a network, particularly the Internet, and a user interface such as a screen 113, possibly touch screen to display the monitoring results to the user.

Those skilled in the art are familiar with algorithms for processing sensor measurements and the associated interfaces, and will know how to implement them in the present system 1.

The casing 120 is secured to the attachment and tightening means 110 by clipping for example (see below).

The casing 120 further comprises electrical connectors, on its coupling face 122 with the coupling face 222 of the capsule 220. Alternatively, the link is done wirelessly between the two modules (bluetooth, infrared, NFC, RFID, etc.).

The second module 200 can comprise a capsule 220 which integrate the microneedles 210. This capsule 220 has the shape of a closed, typically sealed, box which can be coupled with the casing 120. This capsule 220 is interchangeable, which allows obtaining an economical and efficient system, where only the parts said consumables need to be changed. The capsule 220 may have an annular shape, with a through opening 224 in the center. In a variant mentioned above, the sensor is positioned inside the capsule 220 (or in the casing 120) and analyzes the fluid sampled by the microneedles 210.

Likewise, the second module 200 can comprise a patch 250, removably secured to the capsule 220. The patch 250 operates as an adhesive to maintain the penetration of the microneedles 210 into the skin.

In the case of an electrical link with the casing 120, the capsule 220 also comprises electrical connectors 226, on the coupling face 220 with the casing 120, which can cooperate with the electrical connectors of the casing 120. If there is fluid transmission from the second to the first module, then complementary fluid connectors are provided on the capsule 220 and the casing 120.

The second module 200 forms an interchangeable assembly of the system which is chosen according to the desired monitoring type and according to the state of deterioration of the microneedles 210 and/or of the sensor.

Indeed, insofar as the capsule 220 contains the microneedles 210 and/or the sensor, changing the capsule 220 allows changing the sensors if they are at the end of their life or if it is desired to change the measured physical quantity, in a simple, fast and safe handling, without having to throw away other parts (particularly the first module). The capsule 220 needs to be changed infrequently (between weekly and monthly, for example).

Insofar as the capsule 220 minimizes the amount of expensive elements and/or materials (advanced electronic equipment such as a battery or wireless communication means), it is relatively inexpensive.

The Separable Link 300

The separable link 300 is designed to dissociate the two modules 100, 200, that is to say to leave the coupled position, as soon as a tearing threshold is exceeded.

In the coupled position, the second module 200 is housed in the complementary location of the first module 100 and the two modules 100, 200 can exchange data (mainly electrical data thanks to the electrical but possibly fluid connectors). In the free position, the second module 200 is out of the complementary location. When the electrical connection is physical (therefore not wireless), the connection is broken in the free position.

The tearing threshold corresponds to that from which a movement of the system 1 would cause the tearing of the microneedles 210. The force required to remove the microneedles 210 depends, in addition to these per se, on the adhesive force of the patch 250.

The separable link 300 is engaged and disengaged by the effect of a translation. Indeed, any screwing to engage the separable link would prevent the disengagement of the separable link 300 during an involuntary tearing.

The separable link 300 forms a weak link. In this regard, the threshold of tearing of the separable link 300 is chosen between 30 and 400 g, preferably between 70 and 250 g, or between 0.3 and 4 N, preferably between 0.7 and 2.5 N. The tearing is measured by the application of a mass or a force to one of the two modules 100, 200 in a direction orthogonal to the coupling faces, the other module 200, 100 being held fixed (particularly, the mass or the force is applied to one of the elements involved in the separable link).

The separable link is advantageously done between the patch 250 and the first module 100. Thus, the tearing forces move directly through the patch 250, which, by adhering to the skin, will absorb them without transmitting them (or weakly) to the capsule 220 with the microneedles 210.

On the side of the first module 100, the link 300 can be done with a strap (or a bracelet 112) of the means 110, or the casing 120, without particular preference.

Thanks to the separable link 300, it is possible to define in the system 1 a coupled position, in which the first module 100 and the second module 200 are in relation, in particular with the electrical connectors which are in contact. If there is a need to transmit a fluid from the second module 200 to the first module 100, fluid connectors are provided.

In one embodiment, the separable link 300 is produced by a permanent magnet 302. The magnet 302 can be positioned either in the first module 100 or in the second module 200. The other module then comprises a material 304 attracted by the magnet (of the ferromagnetic type or another magnet to improve the holding force). In a variant illustrated in FIG. 2, the magnet 302 and the ferromagnetic material 3004 are respectively positioned in the casing 120 and in the patch 250 (or conversely). The magnet 302 and the ferromagnetic material 304, when the two modules 100, 200 are coupled, face each other.

In one embodiment, the separable link 300 is produced by clipping. A pin (preferably several pins) is (are) then provided on the first or second module 100, 200 and a complementary orifice on the other module, which authorizes the clipping of the pin.

The Patch 250 and the Capsule 220

The patch 250 also comprises an annular shape, with a through orifice 252 in the middle, inside which the capsule 220 is housed. In order to secure both of them to each other, the patch 250 advantageously comprises notches 254 at the wall of the orifice 252 to receive protrusions 228 of the capsule 220.

Around the orifice 252, the thickness of the patch 250 is substantially equal (even equal) to the thickness of the capsule 220 (it is there that part of the removable link 300 is advantageously positioned, such as the magnet 302 or material 304). The patch is also solid (rigid) in this area. In a peripheral area of the patch 250, the latter is finer (flexible) to be able to conform to the shape of the limb. Indeed, in the case of a wrist, the capsule 220 is positioned on a rather flat area of the limb, while the peripheral areas of the patch 250 extend up to the curvature of the wrist.

The Guides 400

Advantageously, the system comprises at least one guide 400 configured to facilitate the natural return to the coupled position of the two modules 100, 200. The guide 400, in some variants, allows defining an intermediate configuration, in which the two modules 100, 200 are not coupled but are engaged via the guide: in other words, there is always a physical contact which is made between the two modules 100, 200 by means of the guide. In the intermediate configuration, if the tearing force ceases, the first module 100 naturally returns to the coupled position thanks in particular to the attachment and tightening means 110 which tend to hold the first module 100 at the point in the intermediate position. When it is desired to completely remove the casing 120, there is a complete disengagement of the casing 120 from the second module 200.

In one embodiment, the guide 400 comprises an inclined side 402, positioned on the first module 100, which cooperates with another inclined side 404 positioned on the second module 200. For reasons of symmetry, the inclined sides 402, 404 are preferably of revolution and form a frustoconical region.

In FIG. 2, the inclined side 402 of the first module 100 is produced in the form of a frustoconical protrusion (like a volcano) extending from the casing 120 (on the side that receives the capsule 220) while narrowing. The inclined side 404 of the second module 200 is produced by a flared opening in the capsule 220, of complementary shape. The flared opening can be the through opening 224 of the capsule 220, so that the volcano comes into contact with the skin: a sensor can then be positioned therein (pulse, etc.). Moreover, the inclined side 402 can be made of a sliding material (such as glass for example) to facilitate the return to the coupled position in a natural way. This guide 400 is structurally independent of the separable link 300.

In one embodiment, not illustrated, the guide is formed by a funnel around the orifice that receives the pin: it then guides the pin towards the clipping orifice.

Thanks to the guide 400 and its inclined sides, when the first module 100 is torn (and when it does not completely exit the guide 400 naturally), it naturally returns to position on the second module. It operates like a three-dimensional mechanical guide (in XZY).

Another guide is described below.

Referring to FIG. 4, several guides 400 can allow a natural return to the coupled position. The guide(s) 400 can for example be implemented by fine rods 404 each entering into a complementary opening 402. The positioning in the coupled position can thus be accurate, whether the first module comprises the attachment and tightening means 110 or not.

Attachment and Tightening Means 110

These attachment and tightening means 110 are typically formed by a strap which can be adjustable or elastic, for example in the form of a bracelet. The attachment and tightening means 110 which can be adjusted for better management of the bearing force exerted on the capsule 220 (via the patch 250) are preferred.

In a preferred embodiment of the attachment and tightening means 110, the attachment and tightening means 110 are autonomous, that is to say they can be mounted on the limb in the absence of the other elements (mainly the casing 120). For that, the attachment and tightening means 110 comprise a strap 112 of sufficient length to go around the limb and a receptacle 114 secured to the strap inside which the casing 120 is housed. The receptacle 114 divides the strap 112 in two branches, each of which is secured to an opposite side of the receptacle 114. The receptacle 114 is for example of generally rectangular shape with rounded corners.

In a preferred embodiment of arrangement of the elements, the receptacle 114 comprises an inner border 116 which defines an opening 117, which allows accommodating at least part of the second module 200. The inner border 116 is housed between the casing 120 and the patch 250 and walls 118. On the casing side 120, the inner border 116 forms a partial bottom on which an outer periphery of the bottom of the casing 120 is housed. The wall 118 may comprise one notch 119 (preferably two), inside which is housed one tab 115 (preferably two) which extend(s) from the casing 120. On the patch side 250, the inner border 116 forms, with the strap 112, a peripheral slot in which part of the patch 250 is located, so that the inner crown 116 is housed between the casing 120 and the patch 250 and thus sandwiched (FIG. 2).

The inner border 116 therefore accommodates an outer area of the patch (thinner than the area around the orifice but rigid, to take up the force of the strap 112) and thus acts as a guide 406 for the replacement of the second module 200 on the first module 100 after the separable link 300 has been disengaged. Likewise, an inner portion of the patch 250, thicker than the outer portion, can be housed inside the border 116. The wall of the border 116 can then abut with the seal and thus acts as a guide (particularly along a plane).

The strap 112 and the receptacle 114 may be integral.

Furthermore, the casing 120 is removably positioned in the receptacle 114, so that the user can keep the following different elements on their wrist:
- the second module 200 alone,
- the second module 200 and the attachment and tightening means 110, without the casing 120 (for example for the swimming pool or the like),
- the first module 100 alone (operation as a connected watch),
- the attachment and tightening means 110 alone (less interest).

Moreover, the removable link between the receptacle and the casing is chosen such that the casing can be easily detached from the receptacle, without snags or shocks. This removable link between the casing 120 and the receptacle 114 can be implemented by a clip, magnets placed on the casing and on the receptacle, and/or a force pin or a force tightening.

The Dock

A recharging dock 3 can be provided, as illustrated in FIG. 3. The dock 3 forms a base capable of receiving the first module 100, and preferably the casing of the first module 100, by replacing the second module 200. The dock comprises the other part of the separable link 300, like the second module 200.

By "removable", it is meant that it can be removed or put back at will.

The invention claimed is:

1. A body analyte monitoring system intended to be attached to a limb of a living being, comprising:
   a first module, comprising attachment and tightening means configured to hold and tighten the system on a limb,
   a second module, comprising microneedles configured to be inserted into the skin to sample and/or analyze a body fluid from the wearer of the body monitoring system when the latter is positioned on the limb,
   the two modules being able to be in coupled position where they are coupled together by shape complementarity,
   wherein the first module and the second module are interconnected by a separable link, the separable link being configured to be released when a tearing threshold is exceeded, the separable link being also reusable, the threshold of tearing of the separable link being lower than the threshold of tearing of the microneedles from the skin, so that once worn, a tearing force disengages the separable link to prevent the tearing of the microneedles from the skin.

2. The body analyte monitoring system according to claim 1, wherein the first module further comprises a casing, to which the attachment and tightening means are attached.

3. The body analyte monitoring system according to claim 2, wherein the attachment and tightening means comprise a receptacle for the casing, the casing being removably attachable in the receptacle.

4. The body analyte monitoring system according to claim 2, wherein the casing is attachable to the second module by the separable link.

5. The body analyte monitoring system according to claim 1, wherein the second module comprises a capsule, which itself comprises the microneedles, and comprises a patch attachable to the capsule, the patch having a skin-adhesive power.

6. The body analyte monitoring system according to claim 5, wherein the patch is securable to the first module by the separable link.

7. The body analyte monitoring system according to claim 5, wherein the patch is removably secured to the capsule, in order to be able to change the patch while keeping the same capsule.

8. The body analyte monitoring system according to claim 1, wherein the attachment and tightening means comprise a strap.

9. The body analyte monitoring system according to claim 8, wherein the strap is made of elastic material.

10. The body analyte monitoring according to claim 9, wherein the strap is in the form of an adjustable bracelet.

11. The body analyte monitoring system according to claim 1, wherein the separable link comprises a magnet.

12. The body analyte monitoring system according to claim 1, wherein the separable link comprises a clipping.

13. The body analyte monitoring system according to claim 1, further comprising at least one guide between the first module and the second module, the guide being configured to allow a natural return to the coupled position.

14. The body analyte monitoring system according to claim 13, wherein the at least one guide comprises a cylindrical or frustoconical shape comprised in the first module and a complementary opening in the second module, the at least one guide defining an intermediate position, in which the frustoconical shape is engaged in the complementary funnel-shaped opening.

15. The body analyte monitoring system according to claim 14, wherein the first module further comprises a casing, to which the attachment and tightening means are attached, and wherein the casing comprises a frustoconical shape and the capsule 220 comprises a flared through opening, of complementary shape.

16. The body analyte monitoring system according to claim 14, wherein the complementary opening is a funnel-shaped complementary opening.

17. The body analyte monitoring system according to claim 1, wherein the threshold of tearing of the separable link has a value between 30 and 400 g.

18. A body analyte monitoring kit comprising a body analyte monitoring system according to claim 2 and a dock configured to receive at least the casing of the first module of the body monitoring device.

19. A body analyte monitoring kit according to claim 18 wherein the dock and the monitoring system form a separable link.

* * * * *